United States Patent [19]

Hinshaw et al.

[11] 4,439,733
[45] Mar. 27, 1984

[54] DISTRIBUTED PHASE RF COIL

[75] Inventors: Waldo S. Hinshaw, Richmond Heights; Robert C. Gauss, Aurora, both of Ohio

[73] Assignee: Technicare Corporation, Solon, Ohio

[21] Appl. No.: 340,134

[22] Filed: Jan. 18, 1982

Related U.S. Application Data

[63] Continuation-in-part of Ser. No. 182,525, Aug. 28, 1980, abandoned.

[51] Int. Cl.³ .............................................. G01R 33/08
[52] U.S. Cl. .................................... 324/322; 324/313; 324/318
[58] Field of Search ............... 324/300, 307, 309, 311, 324/312, 313, 316, 318–320, 322

[56] References Cited

U.S. PATENT DOCUMENTS

3,155,941 11/1964 Mims .................................... 324/316
3,599,120 8/1971 Thibault ............................... 324/318
4,310,799 1/1982 Hutchison ............................ 324/319

Primary Examiner—Michael J. Tokar

[57] ABSTRACT

Apparatus for generating and detecting magnetic field components oscillating at a radio frequency in a direction transverse to a static magnetic field in a nuclear-magnetic-resonance (NMR) system. The apparatus has a plurality of conductive elements spaced from one another and from the axis along which the static magnetic field is directed. The relative amplitudes of alternating currents in the conductive elements are controlled to generate a spatially uniform field. A preferred embodiment uses a standing wave in a coil assembly to control relative current amplitudes, which takes advantage of the current-phase characteristics of such waves. Detection of RF magnetic fields results from an EMF generated in the coil assembly in response to the time-varying magnetic field; the high Q of the coil assembly enhances detection properties.

22 Claims, 11 Drawing Figures

DISTRIBUTED PHASE RF COIL

CROSS-REFERENCE TO RELATED APPLICATIONS

This patent application is a continuation-in-part of U.S. Pat. application Ser. No. 182,525 filed Aug. 28, 1980, now abandoned, in the names of the present inventors and entitled "Distributed Phase RF Coil".

BACKGROUND

This invention relates to apparatus for generating or detecting magnetic field components in a magnetic resonance system. More particularly, the invention relates to improved apparatus suitable for use in a magnetic resonance system for generating or detecting magnetic field components transverse to a line or axis along which a static magnetic field is directed. The term "magnetic resonance system" refers to a system that employs the phenomenon known as magnetic resonance, for example, nuclear magnetic resonance (NMR) typically to determine characteristics of materials placed within the system. The system generates magnetic resonance in the materials by exposure of them to a radio-frequency magnetic field having components transverse to the line or axis along which a static magnetic field is directed.

Magnetic resonance systems generally have employed either solenoid or saddle-shaped radio-frequency coils. The coils are used to generate and/or to detect magnetic field components oscillating in directions transverse to the direction of the static magnetic field.

Magnetic resonance systems have been used for many years in spectroscopic applications for analysis of the atomic or molecular structure or materials placed in the system for examination. When radio-frequency pulses are supplied to an electrical coil surrounding the specimen to be examined, the radio-frequency magnetic-field component transverse to the axis or direction of the static magnetic field can cause the net nuclear magnetic field of the specimen to change in orientation. In the absence of the RF field, the nuclei of the specimen together have a net magnetic field that results from, and that is in alignment with, the static magnetic field in which the specimen is placed. When the RF pulse occurs, the magnetic-field components transverse to the direction of the static magnetic field cause the net magnetic field to change its orientation. The direction of the net magnetic field of the specimen being examined then precesses about the line or axis in the direction of the static magnetic field. This precessing, or time-dependent magnetic field as a result of Faraday's law induces an EMF in an electrical coil or antenna surrounding the specimen. The frequency of precession and of the induced EMF is called the Larmor frequency, is proportional to the strength of the magnetic field to which the specimen is exposed at the time of the precession, and is dependent upon the structure of the nuclei, as well as upon the environment in which the various nuclei are found. Thus, precession of the net magnetic field is magnetic resonance. The frequency of resonance depends upon nuclear structural properties, sometimes called "spin" properties.

The structure or "spin" properties of the nuclei of the various elements that constitute matter vary considerably. Most elements evidence little in the way of detectable magnetic resonance characteristics. Hydrogen produces the strongest NMR response, but other elements, such as phosphorus 31 or carbon 13, also exhibit strong magnetic-resonance responses to RF stimulation in the presence of a magnetic field.

The magnetic resonance phenomenon recently has found application in medical diagnostic-imaging systems. These systems are intended to produce images of the internal structure of the human body. To obtain images of high quality, it is essential that the radio-frequency magnetic field to which the human anatomy is exposed be spatially as uniform as possible in directions transverse to the static magnetic field.

The present invention provides apparatus for generating oscillatory magnetic-field components transverse to the direction of a main static magnetic field. The oscillatory magnetic fields can be, at an RF frequency, spatially uniform while still accommodating the needs of magnetic resonance as applied to imaging of human body structure. Prior art radio-frequency generating and detecting apparatus used in magnetic-resonance imaging systems perhaps is best described in the recent book by Kaufman, Crooks, and Margulis entitled "Nuclear Magnetic Resonance Imaging in Medicine", Igaku-Shoin, New York, 1981, particularly pages 53 through 67 relating to hardware used in NMR imaging.

SUMMARY OF INVENTION

The invention pertains to a system for generating and detecting magnetic resonance in materials. The materials are placed in the system for examination. A magnet in the system provides a static magnetic field directed along a line or axis. The system generates magnetic resonance in the examined materials by exposure of them to a radio-frequency magnetic field having components transverse to the axis. Detectable magnetic-resonance signals also have magnetic-field components transverse to the axis.

The invention provides improved apparatus for generating or detecting the transverse magnetic-field components. The improved apparatus comprises a plurality of conductive elements positioned in spaced relation about the axis along which the static magnetic field of the system is directed. Means are provided for causing alternating currents to flow in the conductive elements, and means also are provided for setting the relative amplitudes of the currents in each of the conductive elements. There is at least one set of current amplitudes alternating at a radio-frequency which is able to generate a composite magnetic field transverse to the axis that is substantially uniform.

The conductive elements of the improved apparatus may include means for interconnecting them with one another in a manner that allows the current amplitudes in the conductive elements to be as stated in the preceding paragraph. In one embodiment of the invention, the means interconnecting the conductive elements comprises sections of transmission line. A standing wave, at a particular frequency, can be made to occur in the plurality of conductive elements interconnected by the sections of transmission line. The standing wave establishes (sets) relative amplitudes of the currents in the conductive elements. This can be made to produce a composite magnetic field, at a radio frequency, that, transverse to the axis of the magnetic-resonance system, is substantially uniform.

The invention may be better understood by reference to the detailed description which follows and to the drawings.

DETAILED DESCRIPTION

Figure 1:
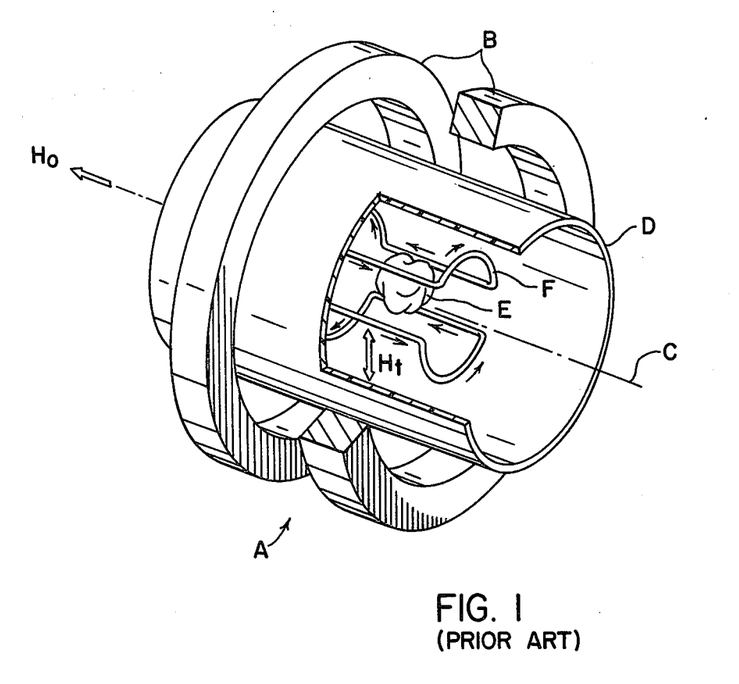
FIG. 1 is a prior art system for generating and detecting magnetic resonance in materials placed in the system for examination.

With reference now to the drawings, wherein like numerals refer to like parts or elements in the several views, there is shown in FIG. 1 a perspective view of the major components of a prior art system that may be used for generating and detecting magnetic resonance in materials placed in the system for examination. The system, generally designated by the letter A, does not illustrate the electronic and computer sub-systems normally required for use in magnetic resonance spectroscopic or imaging applications, but does show the environment in which the improved apparatus of the invention is used. The system of FIG. 1 includes a Helmholtz coil pair B used to generate a large, static homogeneous magnetic field in a direction parallel to a line or axis C. Within a cylinder D of nonmagnetic material, a specimen, or material E may be placed for examination using the magnetic resonance phenomenon previously described. The material E is placed on the axis C and is located within a saddle-shaped coil F.

The direction of the static magnetic field produced by the coil pair B is indicated by an arrow having the designation $H_o$. Currents are made to flow in the radio frequency (RF) coil F having relative directions as indicated by the small arrows adjacent the RF coil elements. The direction of the currents reverse each half cycle of the alternating RF current in coil F. This produces a magnetic field having the direction $H_t$. $H_t$ is of low magnitude compared to $H_o$. The magnitude of the static field $H_o$ may be on the order of several kilogauss.

In magnetic-resonance imaging systems, $H_o$ continually is present while the material E is in the system for analysis or examination. The radio-frequency transverse magnetic field $H_t$ is applied for only a time sufficient to allow the protons in the hydrogen atoms (or the nuclei of other atoms exhibiting the magnetic resonance phenomenon) to be affected such that precession of the net magnetization of the material E occurs. The precession of the net magnetic field associated with the nuclei in the material E occurs at the Larmor frequency, which is directly proportional to the magnitude of the static field $H_o$.

In magnetic-resonance imaging systems, it is necessary to provide various coils (not shown) for producing gradients in the static magnetic field within the region in which the material E to be examined is placed. Usually, these gradient coils are positioned on the surface indicated by the cylinder D, which may be used as a support structure for the gradient coils.

If a human body is to be imaged, using the magnetic resonance technique, then the system shown in FIG. 1 must be of such dimension as to allow a human form to replace the material E to be examined. The human being is introduced into the apparatus on a patient table or similar device that would be made to move along the axis C so that the appropriate portion of the human anatomy is located in the space within the radio-frequency coil F. It is for this reason that the saddle-shaped coil F has been used in prior art systems. If the more conventional solenoid coil were to be used to produce an oscillating RF magnetic field $H_t$ transverse to the axis C, then the axis of the solenoid coil would have to be transverse to the axis C, making it very difficult to introduce the human form into the system of FIG. 1. The space between the Helmholtz pair B could be used for this purpose, but design considerations often preclude a space large enough to accommodate the human form.

The radio-frequency coil F of saddle-shape shown in FIG. 1 is not entirely satisfactory in producing uniform magnetic fields and, due to its physical dimensions, is limited in the maximum frequency of alternating current that can be used to produce images of high quality. The larger the dimensions of the saddle-shaped coils, the greater must be the wavelength of the radio-frequency alternating current if homogeneity of the transverse magnetic field $H_t$ is to be maintained. As a general rule, the wavelength must be no shorter than about ten times the electrical length of the coil; otherwise, phase differences in the coil cause field inhomogeneities to occur. If the system of FIG. 1 is large enough to accommodate the human body, then the saddle-shaped coil must be corresponding large and is limited by electrical phase considerations to the longer wavelengths. However, generally better magnetic resonance imaging and analysis results are obtained with higher static magnetic fields $H_o$ and correspondingly higher Larmor frequency conditions.

The present invention provides improved apparatus for generating or detecting the transverse magnetic-field components $H_t$ in a system of the kind illustrated in FIG. 1. The improved apparatus for generating or detecting magnetic-field components transverse to the line or axis C is hereinafter described in detail, and may be used in place of saddle-shaped radio-frequency coil F or the solenoid coil sometimes used in its place.

Figure 2:
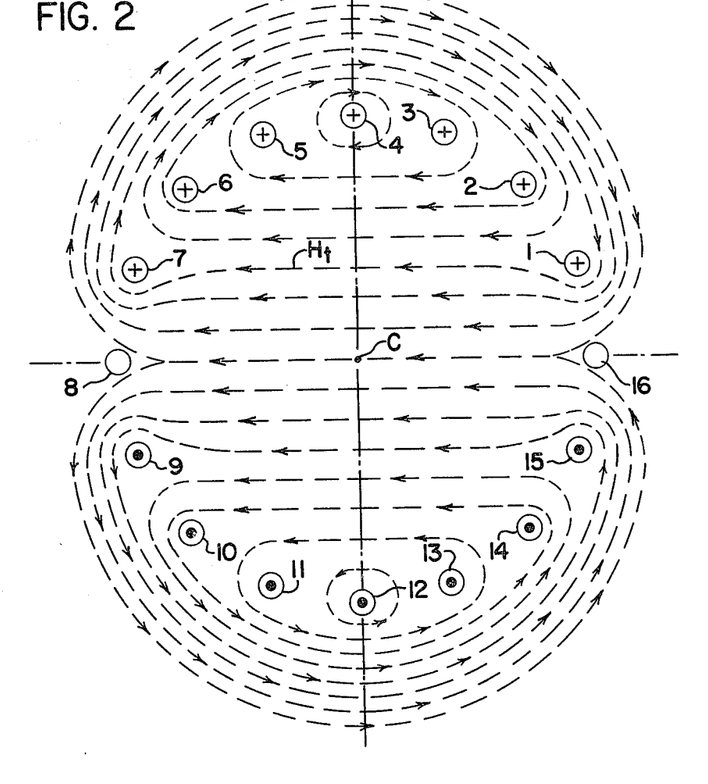
FIG. 2 is a diagrammatic sectional view of a plurality of parallel conductive elements positioned in spaced relation about an axis extending into the plane of the paper.

In FIG. 2, there is shown a cross-sectional schematic representation of a set of sixteen conductive elements positioned in equally-spaced relation about the axis C of a magnetic resonance system. The static magnetic field $H_o$ in FIG. 1 is parallel to the axis C and the conductive elements are made to produce the transverse magnetic field $H_t$ illustrated by the dotted lines and arrows in FIG. 2. The conductors have currents which are designated by crosses and dots. The crosses designate currents in conductive elements 1 through 7, these currents going into the plane of the paper. The dots in the conductive elements 9 through 15 designate currents coming out of the plane of the paper. No current is shown in conductive elements 8 and 16 at the location of the sectional view of FIG. 2.

It is possible, by control of the amplitudes of the various currents in each of the conductive elements, to produce the spatially-uniform magnetic field, transverse to the axis C, shown in FIG. 2. This spatially-uniform magnetic field is made to reverse direction (while remaining transverse to the axis C) by reversal of the directions of the currents in the conductive elements 1 through 7 and 9 through 15 each half-cycle of the alternating current supplied to the conductive elements. The amplitudes of the alternating currents must be controlled relative to one another to produce the spatial uniformity of the magnetic field $H_t$ shown in FIG. 2.

Conductive elements 8 and 16, at the locations in these conductive elements shown in sectional view in FIG. 2, have zero current and such locations thus are current nodes. If the conductive elements 1 through 16 are skewed with respect to the axis C, rather than parallel to this axis, then it may be desirable to have current flow in a portion of these conductive elements to enhance the spatial uniformity of the magnetic field $H_t$.

Figure 3:
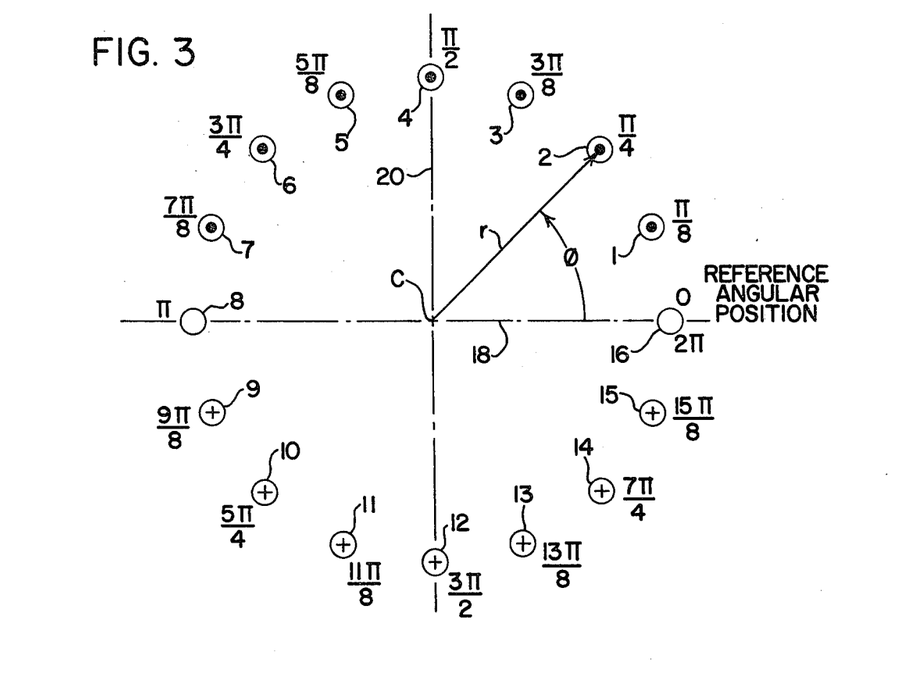
FIG. 3 is a diagrammatic sectional view of the conductive elements of FIG. 2, the dotted magnetic-field lines shown in FIG. 2 having been removed to allow identification of the angular positions of the conductive elements.

In FIG. 3, conductive elements 1 through 16 are shown with the field lines $H_t$ of FIG. 2 removed. The respective angular positions of the 16 conductive elements are designated in radians. The 16th element has a reference angular position of zero or $2\pi$ radians, and conductive element 1 is given the angular position $\pi/8$. Each angular position about the axis C progresses in units of $\pi/8$ radians. Orthogonal center lines 18 and 20 are shown for reference purposes, and the angular position of the conductive elements is designated by the symbol $\phi$. The distance from the axis C of the magnetic resonance system to the conductive elements is indicated by the letter r. Conductive elements 1 through 16 are assumed to extend into the paper in a direction parallel to the axis C, rather than being skewed with respect to this axis. To illustrate current during the other half-cycle of the alternating current, current directions in elements 1 through 7 and 9 through 15 have been reversed with respect to the current directions shown in FIG. 2. The alternating currents produce an oscillating magnetic field $H_t$ transverse to the axis C.

Figure 4:
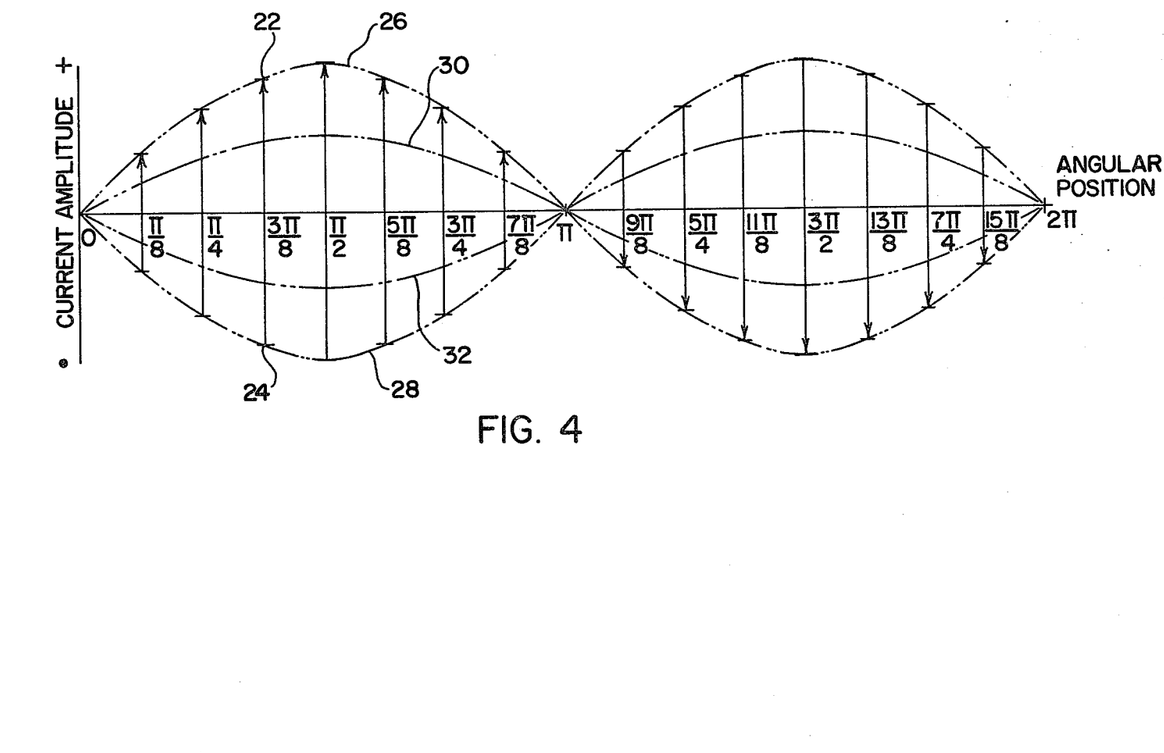
FIG. 4 is a graph of current versus angular position of the conductive elements of FIGS. 2 and 3, and depicts the peak positive and negative values of these oscillating currents, which are able to generate the uniform magnetic field shown in FIG. 2.

FIG. 4 is a graph of the current in the conductive elements of FIGS. 2 and 3 when a spatially uniform magnetic field, having field components transverse to the axis C, is produced. The horizontal axis of the graph of FIG. 4 has designations of angular position from zero to $2\pi$. Current amplitudes in each of the respective 16 conductive elements are represented by vertical lines having arrowheads which indicate peak values of the alternating currents. Conductive element 3 in FIG. 3 is at the angular position $3\pi/8$ in FIG. 4 and has current levels which oscillate in amplitude and direction between the respective positive (+) and negative (.) peak values 22 and 24. The peak values, both positive and negative, of the currents in the respective conductive elements are controlled in amplitude so that the sinusoidal envelopes 26 and 28 are defined by such peak current values. The current values in the various conductive elements are maintained relative to one another in a sinusoidal fashion; at all times, currents in the conductive elements define sinusoidal curves as indicated at 30 and 32. Some deviation from a true sinusoidal envelope for the current-amplitude control may improve homogeneity of the transverse magnetic field. Current nodes exist at angular positions zero ($2\pi$) and $\pi$. These positions are the locations of conductive elements 16 and 8 in FIGS. 2 and 3.

Figure 5:
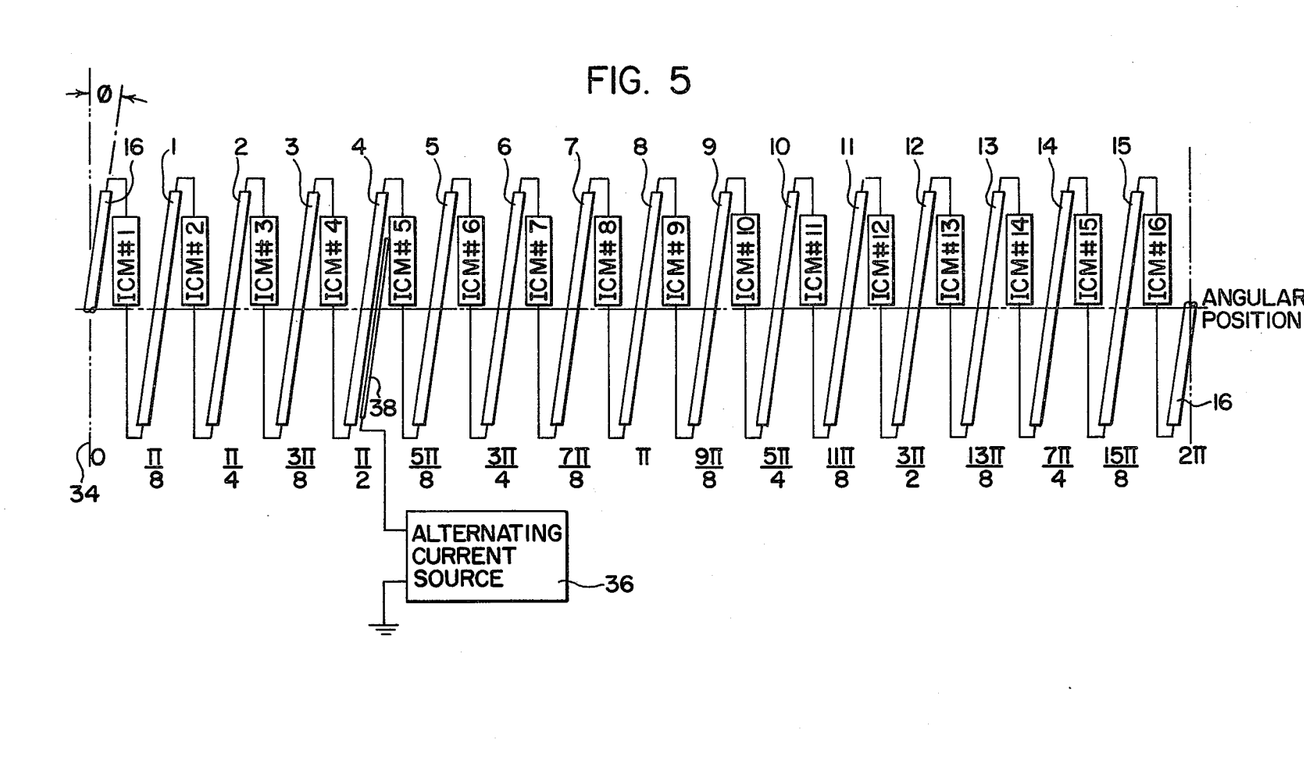
FIG. 5 is a diagrammatic developed view of the conductive elements in FIGS. 2 through 4.
Figure 6:
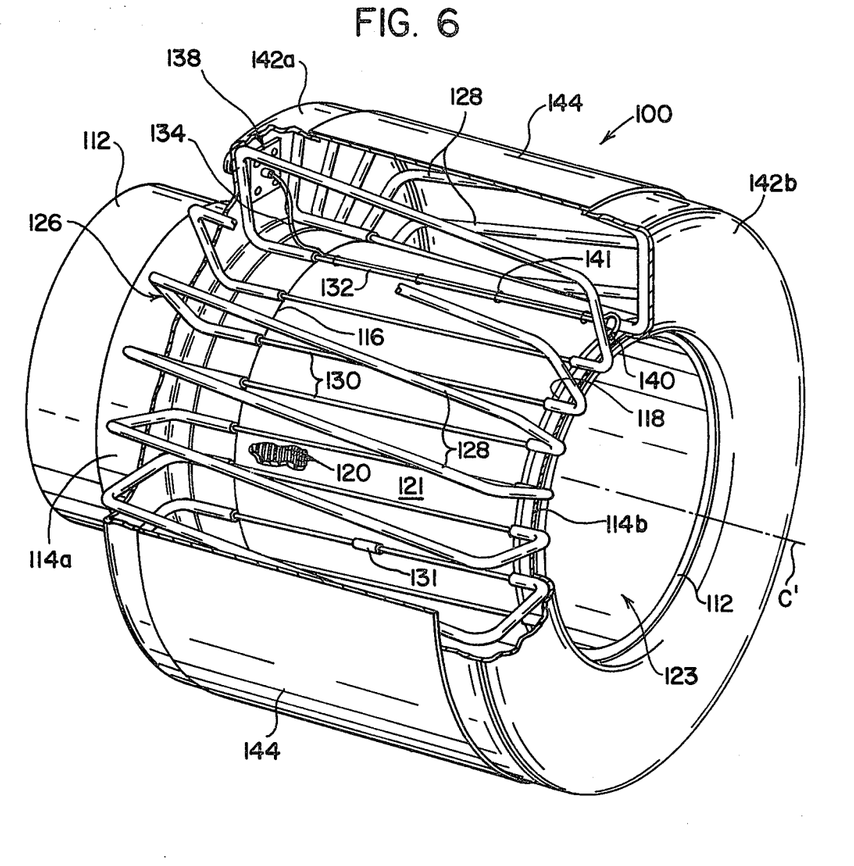
FIG. 6 is a sectional perspective view, on a reduced scale, of an RF coil assembly comprising improved apparatus for generating or detecting transverse magnetic-field components in a magnetic resonance imaging system.

Conductive elements 1 through 16 are shown in FIG. 5 positioned as they would appear if the imaginary cylinder, which the elements define in FIGS. 2 and 3, were cut along the angular position zero and laid out on a flat surface. Conductive elements 1 through 16 are connected together. The means by which the elements are interconnected have interconnecting-means (ICM) designations 1 through 16. Also, elements 1 through 16 are indicated as positioned at an angle with respect to the dot-dash line 34, which is parallel to the axis C. An angle $\theta$ is used to designate the angle between the dot-dash line 34 or axis C and the conductive element. The angle $\theta$ may be zero. If the various means interconnecting conductive elements 1 through 16 in FIG. 5 are capable of causing to be produced in these conductive elements amplitudes of current which satisfy the requirements illustrated in FIG. 4, then a spatially-uniform RF magnetic field having components transverse to the axis C may be generated.

It has been found possible to use sections of transmission line as the means interconnecting the various conductive elements 1 through 16. Also, an alternating current source 36 and a separate conductive feed element 38 may be used to introduce alternating radio-frequency currents into the interconnected conductive elements. It has been found possible to use sections of transmission line, such as sections of coaxial cable or line, as the means for interconnecting the conductive elements. It then is possible to create a standing wave in apparatus of the type diagrammatically illustrated in FIG. 5. If this is done, then the standing wave, which occurs at a particular frequency, may be used to produce the desired radio-frequency, spatially-uniform transverse magnetic field components $H_t$.

As illustrated in FIG. 5, the sixteen interconnecting means connect the conductive elements in a series arrangement. This is not essential. A parallel connection arrangement can be used to interconnect the various conductive elements provided the control of the current amplitudes in the various elements is maintained such that a relationship as illustrated in FIG. 4 is obtained, or, such that some other required control of current amplitude is achieved (as would be the case if the conductive elements were to define an imaginary surface other than a cylinder). However, control of the relative and different current amplitudes in the conductive elements is essential. The current amplitudes may vary in both time and direction, but control of the different amplitudes of these currents in the elements relative to one another is what permits the desired transverse magnetic-field uniformity to be obtained.

If the conductive elements are not positioned to define an imaginary cylinder, as is the case in the conductive-element arrays of FIG. 2 through 4, then it may be desirable to provide control of current amplitudes in the various conductive elements in a manner different than that illustrated in FIG. 4. In FIG. 4, the relative amplitudes are controlled at all times such that the instanteous currents in the array of conductive elements have amplitudes that are sinusoidally related to one another. The current amplitudes, although controlled relative to one another, do vary in both time and direction. An array positioned to define, for example, an imaginary elliptical surface would require somewhat different control of relative current amplitudes to achieve the uniformity of RF magnetic field illustrated in FIG. 1.

If the various interconnecting means of FIG. 5 connect the array of conductive elements in parallel, rather than serially as illustrated, then the interconnecting means may comprise sources of electrical energy. Various techniques and equipment known in the electrical arts could be used to generate currents of different amplitudes in the array of conductive elements. For example, the conductive elements could be connected in parallel across the supply leads of a source of electrical energy and could be made to have different electrical impedances so that the current amplitudes in the various conductive elements are controlled relative to one another. Alternatively, the actual conductive elements could have identical electrical impedances, but could be coupled to the source of RF electrical energy through impedances which vary from one conductive element to the next.

With particular reference now to FIGS. 6 through 10, there is illustrated an embodiment of the invention which comprises apparatus for generating or detecting field components in a magnetic resonance system. The apparatus is designed to generate a "standing wave" at a particular frequency of oscillation. The apparatus has a plurality of conductive elements positioned in spaced relation, and the conductive elements are interconnected by means for setting the amplitudes and controlling the phase angles of the currents in the conductive elements of the apparatus. The interconnecting means comprises sections of coaxial transmission line.

Figure 7:
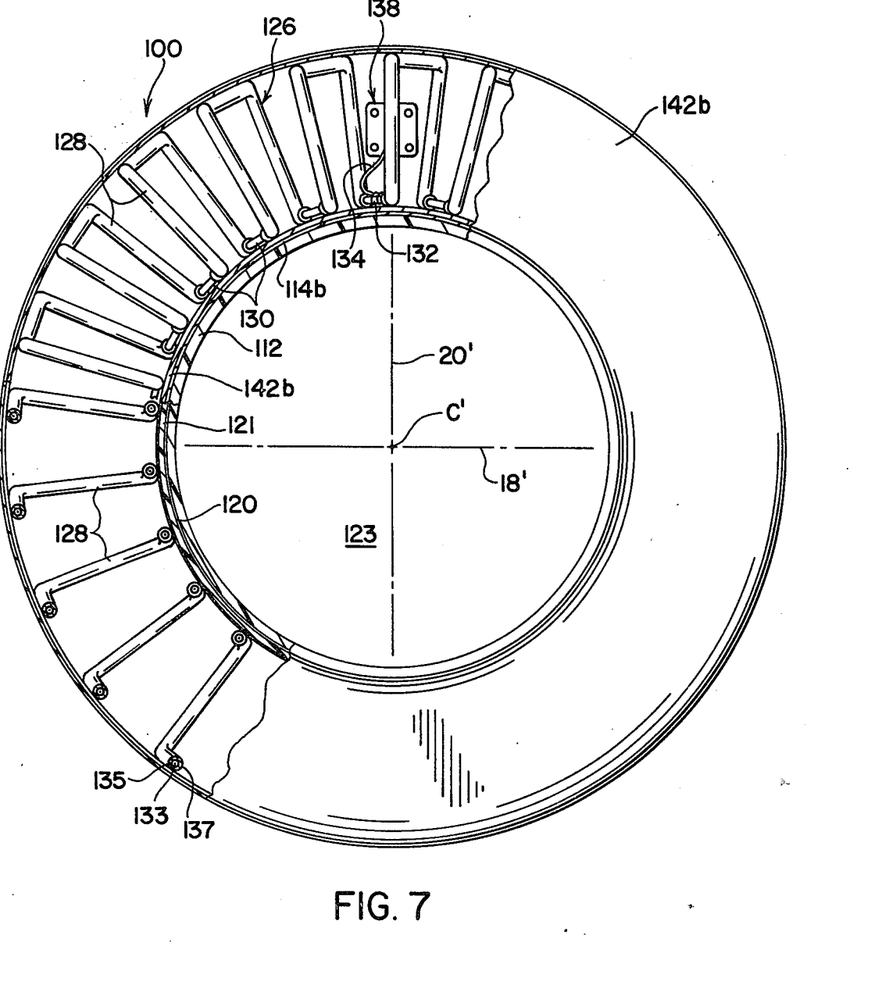
FIG. 7 is an elevational view, partially in section, of the coil assembly of FIG. 6.

A currently-preferred apparatus for generating or detecting the transverse magnetic-field components in a magnetic resonance system is of the general type illustrated in detail in FIGS. 6 through 10. The design details vary with application, strength of the static magnetic field (which affects the frequency at which the apparatus must produce a standing wave), and with dimensional requirements in the NMR system. The apparatus illustrated is intended for imaging of the human head. It comprises a coil assembly generally designated by the numeral 100. The coil assembly has an axis C' which, when used in the magnetic resonance system, would coincide with the axis C of FIG. 1. Similarly, axes 18' and 20' are othogonal to each other and to the axis C', as shown in FIG. 7.

Figure 8:
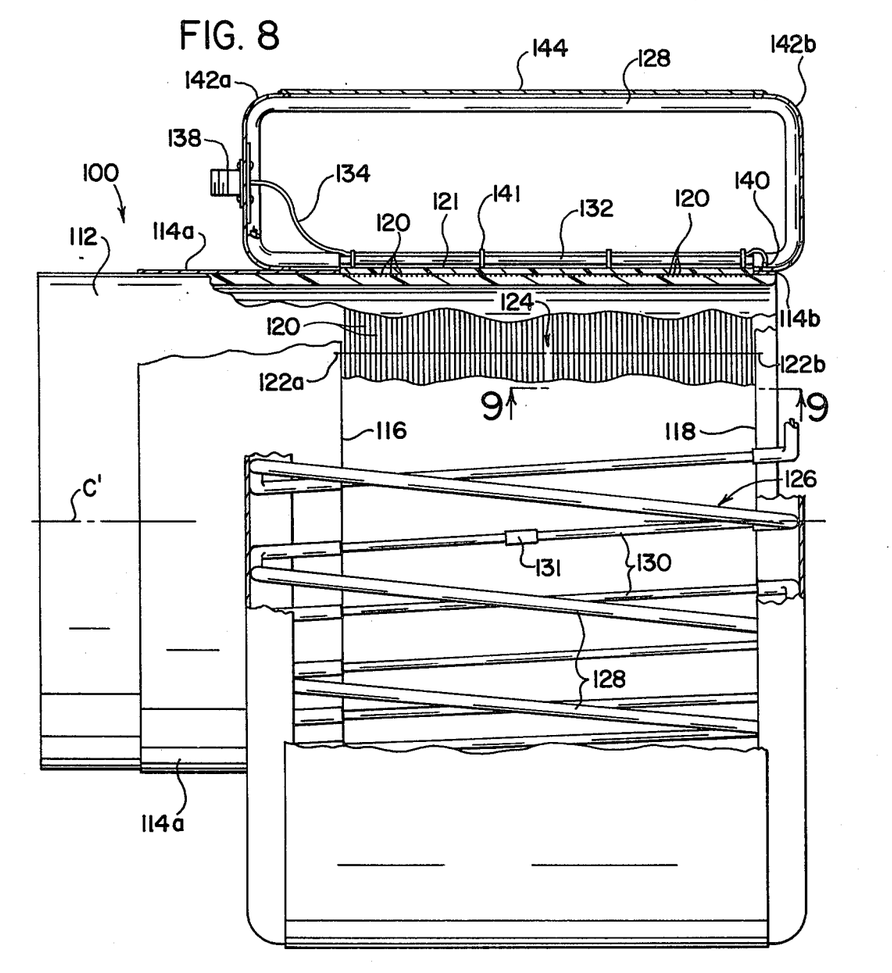
FIG. 8 is a longitudinal sectional view of the coil assembly of FIGS. 7 and 8.
Figure 9:
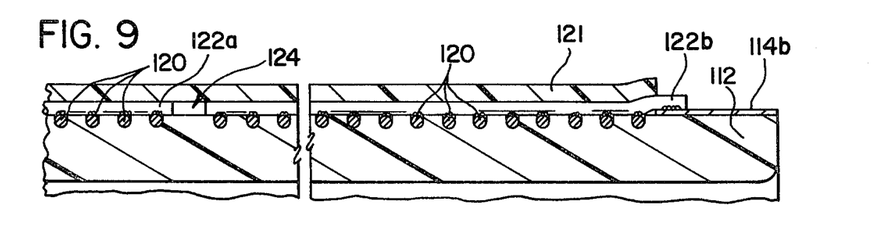
FIG. 9 is a partial sectional view, taken along the line 9—9 in FIG. 8 and is on an enlarged scale illustrating details of the construction of the coil assembly.
Figure 10:
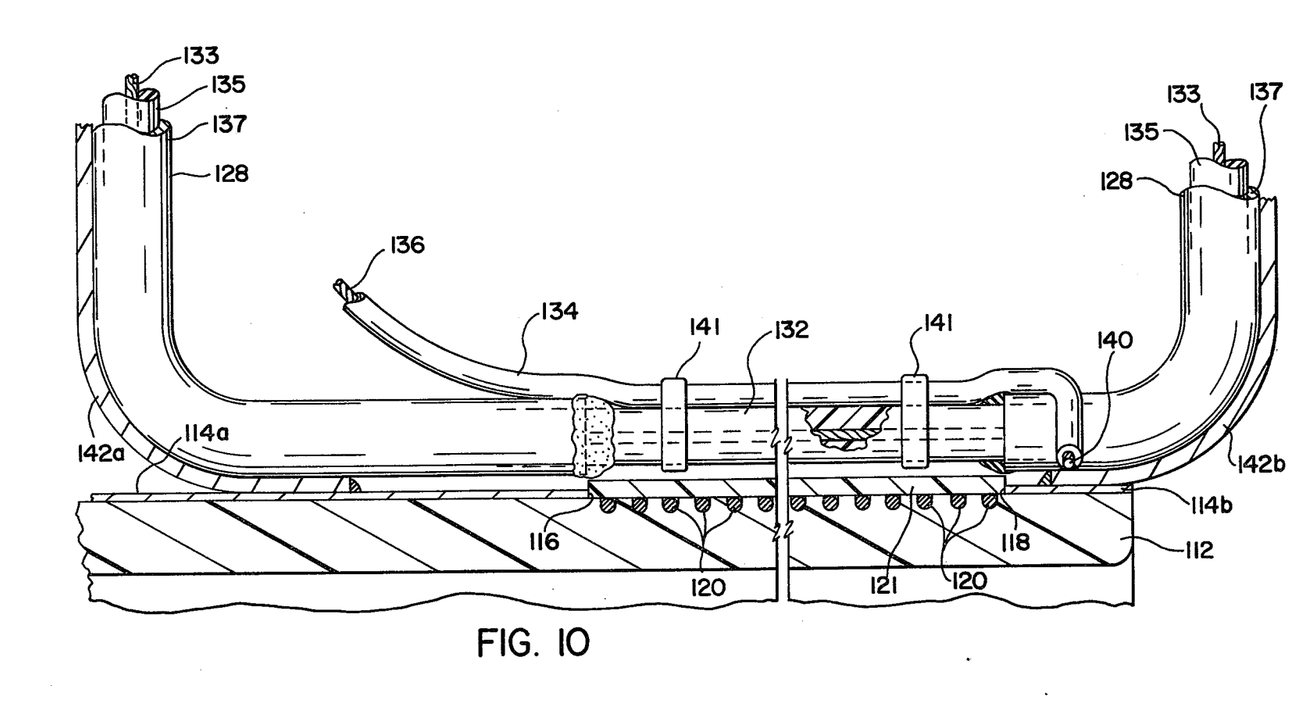
FIG. 10 is an enlarged view, partially in section, illustrating one of the conductive elements of the coil assembly and means for coupling or causing alternating radio-frequency currents to flow in the conductive elements of the coil assembly.

The coil assembly 100 includes a coil support or form 112, which is formed from an insulating and nonmagnetic material, such as polyethylene, nylon, glass or other material substantially uneffected by radio-frequency energy. Conductive sheet metal, preferably made from soft copper or brass is wrapped around the coil support in two strip portions located at opposite ends of the coil form. The first of these is designated 114a and the second is designated 114b. Intermediate these two conductive strips 114a and 114b is a region bounded by the circular edges 116 and 118 of the respective conductive strips. As may be seen in FIG. 6, conductors 120 are contained in the space between the edges of 116 and 118 and are covered with a Teflon or other nonconductive sheet material 121. The conductive elements 120 act as a Faraday shield, which prevents radio-frequency electric fields from entering the bore 123 of the coil assembly. The conductors 120 are located in grooves cut in the outer surface of the coil support 112. These grooves may be helically cut with a lathe or other suitable machine, and the conductors 120 may be a continuous element wound within the grooves. As is best seen in FIGS. 9 and 10, conductors 122a and 122b are placed in electrical contact with the conductors 120 to short the helical turns together. A gap 124, which may be seen in both FIGS. 8 and 9, is located between the conductors 122a and 122b. The helical winding forming conductors 120 also has a gap (not shown). The purpose of the gaps is to prevent the existence of a conductive path parallel to the axis C' of the coil assembly 100. An oscillating field could induce currents in such a conductive path with undesirable result.

The Faraday shield comprising the conductors 120, 122a, and 122b prevents electric fields from entering the bore 123 of the coil assembly, but allows magnetic fields directed transverse to the axis C' freely to enter the bore region. It is in the bore 123 that the material or anatomical part to be examined is placed. The coil assembly 100 is particularly intended for magnetic-resonance imaging of the human head and, thus, has an internal diameter of approximately 28 centimeters and is designed to be operated at approximately 6.2 MHz. Because it is desirable to have the bore diameter of the coil only slightly larger than the size of the anatomical portion to be examined, the size and construction details of the optimum coil assembly will differ in accordance with application. The design also will vary depending upon the strength of the static magnetic field to be used in the magnetic resonance system and upon the desired radio frequency.

The most important feature of the coil assembly of FIGS. 6 through 10 is the provision of a plurality of conductive elements positioned in spaced relation about the axis C' or C of the imaging system illustrated in FIG. 1. Also, means must be provided for causing alternating currents to flow in the conductive elements. Additionally, means must be provided for setting the relative amplitudes of the currents in each of the conductive elements so that the components of the magnetic field transverse to the axis C' or C of the imaging system can be made substantially uniform, as illustrated in FIG. 1. Such control is achieved by use of the generally toroidallyshaped coil 126. Coil 126, in conjunction with the entire apparatus 100 and when coupled to a suitable source of RF electrical energy, has at least one set of current amplitudes in the conductive elements 130 thereof which generate a composite magnetic field, transverse to the axis, that is substantially uniform. The current amplitudes of the set may vary in amplitude together as a function of time, but a predetermined relationship is maintained between the current amplitudes so that the uniform transverse field results.

Coil 126 has conductive elements 130, which are active in generating the composite magnetic field. Sections of coaxial transmission line 128 interconnect the conductive elements 130, and are the means used to set the relative amplitudes of the currents in each of the conductive elements 130.

The conductive elements 130 extend between the edges 116 and 118 of the conductive strips 114a and 114b on the coil support 112. Conductive elements 130 actually may comprise the center conductor of a coaxial line from which the outer conductor has been removed in the region between 116 and 118. The center conductor of the coaxial cable in the coil 126 forms an electrical closed-loop, as is indicated at junction 131 in FIG. 8. At junction 131, the center conductor of the coaxial transmission line forming the coil 126 has its opposite ends butted together, soldered, and preferably coated with a nonconductive dielectric material, such as silicone rubber. An insulating sleeve is placed over the junction to provide additional electrical isolation.

Radio-frequency energy may be introduced into the coil 126 and, thus, into the coil assembly 100, to produce a radio-frequency magnetic field within the bore 123. Inductive or electric-field coupling techniques may be used for this purpose. Inductive coupling is the currently-preferred method of feeding radio-frequency energy into the coil assembly. A conductive element 132, shown in an enlarged view in FIG. 10, is one of the conductive elements 130 of the coil assembly and has a center conductor 133 surrounded by a dielectric material 135. The dielectric material separates center conductor 133 from the outer conductor 137 of the coaxial line. In the region between the edges of 116 and 118, the aforementioned active region with respect to magnetic field generation in the bore 123, the outer conductor 137 is removed. This is the case with all of the conductive elements 130 and removal may be accomplished by etching away of the outer conductor, which preferably is formed from copper tubing. Inductive coupling to the conductive element 132 is achieved with the use of an insulated conductor 134 having a conductive element 136 that enters the coil assembly 126 through a coaxial coupling device 138. The conductive element 134 is soldered at 140 to an end shield 142b.

In FIG. 10, it may be seen that straps 141 of dielectric material maintain the conductive element 134 in fixed relationship to the conductive element 132. Radio-frequency energy introduced into the coaxial connector 138 causes current to flow through the conductor 136 to the end shield 142b to which the conductor 136 is connected at 140. This current oscillates at a radio frequency and, due to its inductive coupling to the portion of conductor 133 in conductive element 132 between points 116 and 118, causes current to fllow in conductor 133.

The end shield 142b is soldered to, and in electrical contact with, the conductive strip 114b. Similarly, an end shield 142a at the opposite end of the coil assembly is soldered to, and in electrical contact with, the conductive strip 114a. The various end portions of the turns forming the coil 126 are positioned in the end shields 142a and 142b. The end shields, in conjunction with a cylindrical piece of conductive material 144 surrounding the coil 126, shield the coil from external fields. Conductive sheet 144 is in contact electrically with the end shields 142a and 142b, as well as with the outer conductors of each of the coaxial transmission line sections 128. Thus, the coil assembly 100, is shielded on its exterior portions by the end shields 142a and 142b, the outer cylindrical shield 144, and within the bore 123, by the Faraday shield conductors 120.

The coil 126 may be regarded as being comprised of a plurality of substantially parallel first conductive elements 130 and a plurality of second or interconnecting conductive elements 128. Conductive elements 130 are separated from one another by the interconnecting second conductive elements 128, which are sections of coaxial tranmission line having an inner conductor 133 and an outer conductor 137. The outer conductor 137 confines the electric and magnetic fields associated with current in the second conductive elements 128 and prevents them, to a substantial degree, from interacting with the magnetic fields associated with currents in the conductive elements 130. This is true even though the conductive elements 130 in fact are the center conductor of the sections of coaxial tranmission line. Likewise, in the coaxial sections 128, the electric field is confined to the region between the center conductor 133 and the outer conductor. However, in the active region between edges of 116 and 118 of the conductive strips 114a and 114b, the electric and magnetic field is permitted to enter the spaces between the conductive elements 120 of the Faraday shield and enter into the bore 123 of the coil assembly 100.

The electric field associated with current in the conductive elements 130, rather than being limited by the interior of the outer conductor of the coaxial elements 128, is bounded by the interior of the conductive sheet or shield 144 surrounding the coil assembly. Thus, the interior of the conductive strip 144 forms a "ground plane" with respect to transmission of electrical energy in the active region between the ends of each of the interconnecting coaxial-transmission-line sections.

The coil assembly 100 has 24 turns in its toroidal winding 126. This means it has 24 substantially parallel first conductive elements 130 and a corresponding number of second, interconnecting sections of transmission line 128. The coil assembly 100 as a whole will have a frequency at which it will be electrically resonant. If the coil assembly is excited at this frequency, a standing wave is produced within the coil assembly 100. If the conductive elements 130 are uniformly spaced and of equal length and if the interconnecting sections of coaxial transmission 128 are uniformily positioned and of equal length, then the composite magnetic field within the bore 123 will be uniform in magnitude as to its components transverse to the axis C'. This magnitude will vary with time and will reverse in direction twice each cycle of the radio-frequency energy being supplied to the coil.

Coil assembly 100 can be used to detect radio-frequency signals that are generated by a material located within its bore 123. The high Q of the coil assembly makes it very sensitive to magnetic resonance signals.

At the resonant frequency of the coil assembly 100, the closed-loop electrical path of the coil 126 is one wavelength long. This closed-loop electrical path is comprised of all of the conductive elements 130 and interconnecting sections of coaxial transmission line 128. A current maximum occurs at or near the conductive element 132, the location at which the incoming radio-frequency electrical energy is introduced. A corresponding current maximum is located in the conductive element diametrically opposite. Current nodes occur in the two diametrically-opposed conductive elements located intermediate the elements having the current maximums.

The length of the closed-loop electrical path within the coil assembly 100 is approximately 30% less than it would be if the velocity of propagation of the RF electrical energy in the electrical path were equal to the speed of light. In other words, the velocity of propagation of the energy in the coil assembly 100 should be regarded as approximately 30% less than that of the velocity of light. The propagation velocity is influenced by the medium through which the radio-frequency energy is propagated. The dielectric layer on the conductive elements 133 and in the coaxial transmission line reduces the propagation velocity from the free-space velocity. Also, the spacing between the conductive elements 130 and the substantially parallel sections of coaxial line 128 has an effect on the frequency at which resonance occurs in the coil assembly 100. Since this resonant frequency determines the condition under which the desired uniform field is achieved in the bore 123 in magnetic resonance applications, and since this must be related to the strength of the static magnetic field in the magnetic resonance system, the design of the coil assembly 100 is important. To satisfy design requirements, the number of electrical turns in the coil 126 may be varied as necessary to achieve a single wavelength, at the desired frequency, in the electrically closed loop forming the basis of the coil assembly.

Conductive elements 130 and sections 128 are shown as being of respectively uniform size and are equallyspaced in the coil assembly 100. This is not essential. Each of the conductive elements, under the standingwave or resonant electrical condition, have currents in them which are set or controlled by their respective positions in the single wavelength surrounding the axis C'. With respect to FIG. 4, which illustrates the current in a standing wave, it may be seen that the conductive elements 130 could be located at angular positions that are not uniform relative to one another. In such case, the interconnecting sections of coaxial transmission line would have to be of different length or transmission characteristics and the conductive elements would have to be positioned such that the currents in them will, at a predetermined frequency, satisfy the requirements for existence of a standing wave.

The coil assembly 100 has inductance and distributed capacitance (and possibly external capacitance). The conductive elements 130 are interconnected by transmission line or delay line sections 128 which, together with the conductive elements, constitute a closed-loop electrical path. Due to this construction, coil assembly 100 may be regarded as a "resonant cavity", that is, as a device that is resonant at an electrical frequency.

There exists a frequency of electromagnetic energy which, when inductively coupled to the coil assembly 100, causes the appearance of a standing wave in the coil assembly. The currents in the conductive elements 130 have amplitudes relative to one another as required for the existence of a standing wave. The conductive elements of the coil assembly are positioned to generate a composite magnetic field that, when the standing wave exists, is substantially uniform transverse to the axis of the assembly.

Each of the conductive elements 130 could be driven with a separate source of electrical energy. These separately driven elements could be individually tuned to be resonant at a frequency and, individually or collectively, could be used to generate a composite magnetic field as stated above. The individually tuned elements also could be used to detect magnetic fields inductively coupled to the elements and oscillating at the frequency to which the elements are tuned. Collectively, the elements could be regarded as a "resonant cavity" due to their mutual inductance.

The structure of the coil assembly 100 provides the required control of relative current amplitudes and has the advantage of simplicity over separately driven conductive elements. The means 128 interconnecting the conductive elements 130 are phase-delay lines that allow a standing wave to exist with the relative current amplitudes in the conductive elements then being as required for the production of the desired uniform field. The coil assembly has a high ratio of inductive reactance to resistance, which is regarded as a quality factor Q for an inductive device. The Q of an inductor in a resonant circuit, such as the "resonant cavity" coil assembly, determines the ability of the inductor to discriminate signal levels at the resonant frequency from corresponding signal levels at other frequencies. Because of the very low signal levels that must be detected in magnetic resonance systems, the Q of the coil used in RF signal detection is of considerable importance.

In FIG. 5, there is shown the angle $\theta$ which the conductive elements form with respect to the axis C of the imaging system and array. The conductive elements 130 in the coil assembly 100 also have such an angle $\theta$ with respect to axis C'. The reason for this is that the standing wave in the coil assembly 100 has one wavelength in the total conductive electrical loop surrounding the axis C'. This means that there is a phase difference in the current between the ends of each of the conductive elements 130, as there is in any transmission line on which there is a standing wave. The angle $\theta$, therefore, should be equal to the electrical phase difference in the standing wave which occurs over the length of the conductive element positioned at such angle.

Figure 11:
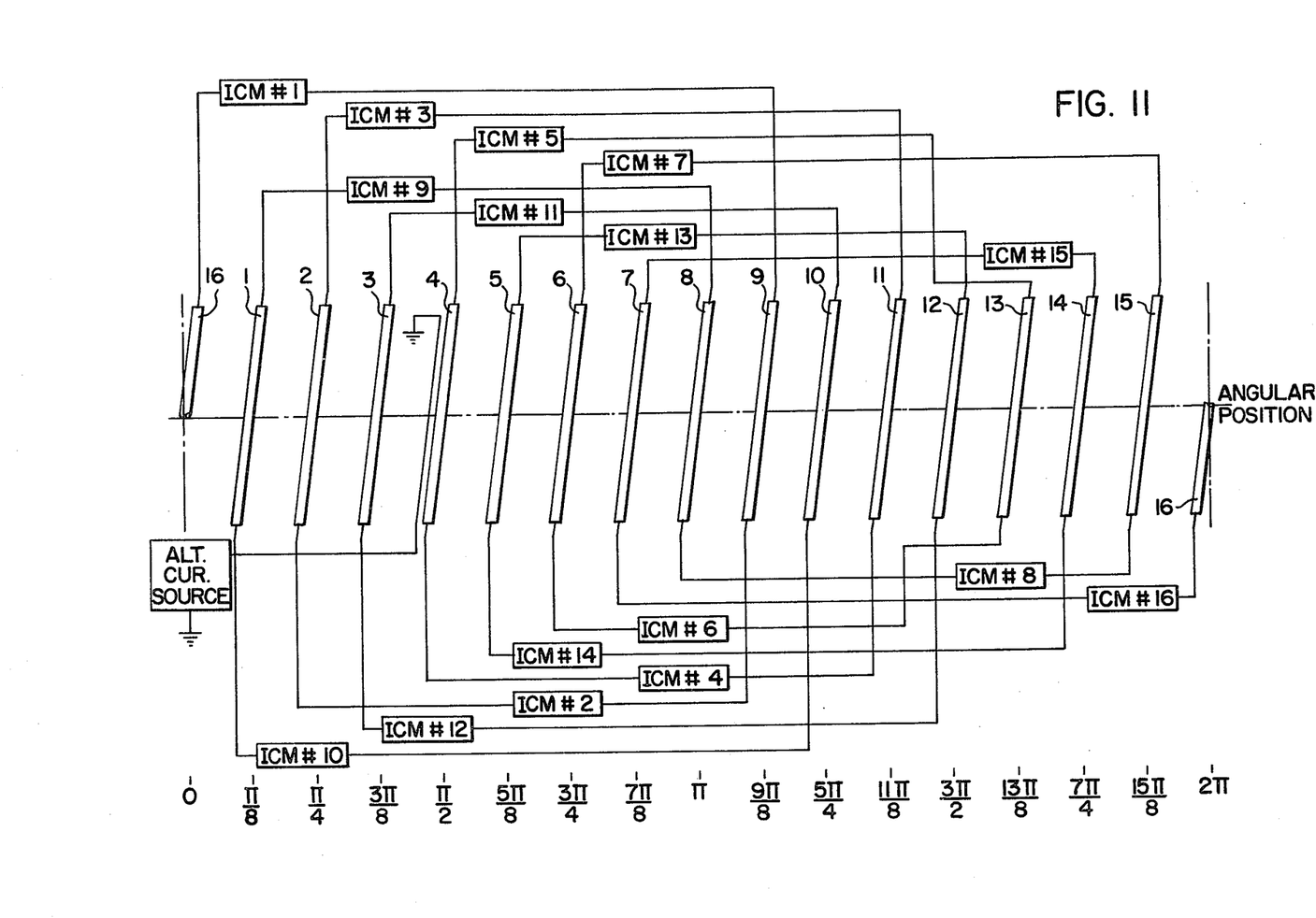
FIG. 11 is a diagrammatic view similar to FIG. 5, but has means interconnecting the conductive elements of the array in a structurally different, but functionally-similar way.

In FIG. 11, there is shown a diagrammatic view, similar to FIG. 5, of an array of sixteen substantially parallel conductive elements having sixteen means (ICM #1 to ICM #16) interconnecting the elements of the array. The interconnecting means can be sections of coaxial transmission line, as in the coil assembly of FIG. 6-10, but the coaxial sections need not be in the generally toroidal form of coil 126. Instead, the respective sections of coaxial line can interconnect the corresponding ends of two conductive elements which are separated in angular position by ' radians plus or minus an offset angle of $2\pi$ radians divided by the number of conductive elements in the array. Otherwise stated and for the array of FIG. 11, the coaxial lines would interconnect corresponding ends of conductive elements separated by an angle of either $(\pi + 2\pi/16)$ radians or $(\pi - 2\pi/16)$ radians. This, simplified, is a separation angle of either $7\pi/8$ or $9\pi/8$. If the coaxial transmission-line sections ICM were of electrically different lengths, then the angular-position separations would be as required to allow a standing wave to generate a spatially-uniform magnetic field.

Based upon the foregoing description of the invention, what is claimed is:

1. In a system for generating and detecting magnetic resonance in materials placed in the system for examination, the system having a magnet for providing a static magnetic field directed along a line or axis, the system generating magnetic resonance in the materials through their exposure to a radio-frequency magnetic field having components transverse to the axis, improved apparatus for generating or detecting the radio-frequency magnetic field, the improvement comprising:
(a) a plurality of conductive elements positioned in spaced relation about the axis;
(b) means for causing alternating currents to flow in the conductive elements; and
(c) means for setting the relative amplitudes of the currents in each of the conductive elements, there being at least one set of current amplitudes, generally different from one another and alternating at a radio frequency, which is able to generate a composite magnetic field transverse to the axis that is substantially uniform.

2. Apparatus according to claim 1, wherein the means for setting the relative amplitudes of the currents comprises means for controlling the amplitudes of the currents in the conductors relative to one another and for controlling such amplitudes in relation to the positions of the respective conductive elements about the axis.

3. Apparatus according to claim 2, wherein the means for setting the relative amplitudes of the currents comprises means for interconnecting the conductive elements, the interconnecting means and the conductive elements together forming an electrical closed-loop, the electrical closed-loop sustaining a standing wave when coupled to a source of electrical energy oscillating at the radio frequency.

4. Apparatus according to claim 3, wherein the interconnecting means comprises means for causing the amplitudes of the currents in the interconnected conductive elements to differ when the apparatus is coupled to a source of electrical energy oscillating at the radio frequency.

5. Apparatus according to claim 4, wherein, when the apparatus is coupled to a source of electrical energy oscillating at the radio frequency to sustain the standing wave, the sum of the phase-angle differences across the conductive elements and the phase-angle differences across the interconnecting sections total $2\pi$ radians.

6. Apparatus according to claim 5, wherein the means for setting the relative amplitudes of the currents in the interconnected conductive elements comprises sections of transmission line, the sections of transmission line separating the conductive elements from one another.

7. Apparatus according to claim 6, wherein the sections of transmission line include means for limiting interaction of magnetic fields associated with currents in the sections of transmission line with magnetic fields associated with currents in the conductive elements.

8. Apparatus according to claim 6, wherein the sections of transmission line include an inner conductor and an outer conductor, the inner conductor being integral with the conductive elements of the apparatus, and the outer conductors of the sections of transmission line being spaced from the inner conductor and substantially confining magnetic fields associated with currents in the transmission line sections to the region between the inner and outer conductors.

9. Apparatus according to claim 7, wherein the conductive elements define a surface of revolution.

10. Apparatus according to claim 7, wherein the conductive elements define a cylindrical surface.

11. Apparatus according to claim 10, wherein the conductive elements are substantially parallel with the axis of the cylinder.

12. Apparatus according to claim 10, wherein the conductive elements are skewed with respect to the axis of the cylinder.

13. A coil assembly for either exciting a material undergoing magnetic resonance analysis with the use of an oscillating radio-frequency magnetic field or for detecting such magnetic fields as a result of the magnetic resonance of such material, the coil assembly comprising:
(a) a coil support defining a region within the support in which a material to be examined may be placed; and
(b) a substantially toroidally-shaped coil peripherally positioned about the coil support, the coil having alternating sections of conductive elements separated by sections of coaxial transmission line, the conductive elements being the center conductor of the sections of coaxial transmission line, and the conductive elements between the sections of coaxial transmission line being substantially parallel to the axis of the coil support.

14. A coil assembly according to claim 13, which further comprises a pair of end shields and a cylindrically-shaped conductive sheet interconnecting the end shields, the toroidally-shaped coil being enclosed by the end shield and the conductive sheet.

15. A coil assembly according to claim 14, which further comprises means for inductively coupling radio-frequency electrical energy to one of the conductive elements of the toroidally-shaped coil.

16. A coil assembly according to claim 15, wherein the means for coupling the radio-frequency energy comprises a conductor positioned parallel to one of the conductive elements of the toroidally-shaped coil.

17. A coil assembly according to claim 14, wherein the toroidally-shaped coil makes one revolution about the axis of the coil support.

18. A coil assembly according to claim 17, wherein the toroidally-shaped coil has a conductor which forms an electrical closed loop.

19. A coil assembly according to claim 13, wherein sections of coaxial transmission line interconnect corresponding ends of conductive elements separated by angular positions about the axis, the separation being equal in radians to $2\pi$ plus or minus the quantity $2\pi$ divided by the number of conductive elements thus interconnected.

20. A coil assembly according to claim 13, wherein the sections of coaxial transmission line interconnect opposite ends of adjacent conductive elements positioned about the axis of the coil support.

21. A coil assembly according to either of claims 19 or 20, wherein the conductive elements are equally-spaced from one another about the axis of the coil support.

22. A coil assembly according to claim 13, wherein the sections of transmission line are of such length, and the conductive elements are positioned about the axis of the coil support, such that an oscillating magnetic field transverse to the axis exists when the coil assembly is excited by an RF electrical signal having a wavelength in the coil assembly equal to its electrical length.

* * * * *